(12) United States Patent
Gyertyan et al.

(10) Patent No.: US 8,263,773 B2
(45) Date of Patent: Sep. 11, 2012

(54) THIENO [2,3-B] PYRIDINE COMPOUNDS WITH MGLUR ACTIVITY

(75) Inventors: Istvan Gyertyan, Budapest (HU); Katalin Nogradi, Budapest (HU); Ottilia Elekes, Budapest (HU); Monika Vastag, Budapest (HU); Amrita Agnes Bobok, Budapest (HU); Katalin Saghy, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 380 days.

(21) Appl. No.: 12/490,527

(22) Filed: Jun. 24, 2009

(65) Prior Publication Data

US 2009/0326002 A1    Dec. 31, 2009

Related U.S. Application Data

(60) Provisional application No. 61/076,006, filed on Jun. 26, 2008.

(51) Int. Cl.
*A61K 31/4436*    (2006.01)
*C07D 513/04*    (2006.01)

(52) U.S. Cl. ........................................ 546/114; 514/301

(58) Field of Classification Search ........................ None
See application file for complete search history.

(56) References Cited

FOREIGN PATENT DOCUMENTS

WO    WO 2007/072095    6/2007

OTHER PUBLICATIONS

West, Anthony R., "Solid State Chemistry and its Applications", Wiley, New York, 1988, pp. 358 & 365.*
Fox and Threlfall, "2,3-Diaminopyridine," *Org. Synth. Coll.*, 1973, 5:346-351.
Gasparini et al., "[$^3$H]-M-MPEP, a Potent, Subtype-Selective Radioligand for the Metabotropic Glutamate Receptor Subtype 5," *Bioorg. Med. Chem. Lett.*, 2002, 12:407-409.
Klemm et al., "Chemistry of Thienopyridines. VIII. Substitution Products Derived from Thieno[2,3-b]pyridine 7-Oxide," *J. Heterocycl. Chem.*, 1970, 7:81-89.
Vogel et al., "A simple and reliable conflict procedure for testing anti-anxiety agents," *Psychopharmacology (Berl.)*, 1971, 21:1-7.

* cited by examiner

*Primary Examiner* — David K O Dell
(74) *Attorney, Agent, or Firm* — Fish & Richardson P.C.

(57) ABSTRACT

Provided herein are Thieno[2,3-b]pyridine compounds with mGluR activity. Also provided herein are processes and intermediates for the preparation of the Thieno[2,3-b]pyridine compounds, pharmaceutical compositions containing these compounds, and the use of these compounds in treatment, therapy, and/or prevention of conditions which require modulation of mGluR1 and mGluR5 receptors.

16 Claims, No Drawings

THIENO [2,3-B] PYRIDINE COMPOUNDS WITH MGLUR ACTIVITY

CROSS-REFERENCE TO RELATED APPLICATIONS

This application claims priority to U.S. Provisional Application Ser. No. 61/076,006, filed on Jun. 26, 2008, which is incorporated by reference in its entirety herein.

FIELD OF THE INVENTION

The present invention relates to mGluR1 and mGluR5 receptor subtype preferring ligands of formula (I) and/or salts and/or hydrates and/or solvates thereof, to the processes for their preparation, to pharmaceutical compositions containing these compounds and to their use in treatment, therapy and/or prevention of a condition related to modulation of mGluR1 and mGluR5 receptors.

BACKGROUND OF THE INVENTION

Int. Pat. Appl. WO 2007/072095 discloses thieno-pyridine derivatives that are mGluR1 and mGluR5 receptor subtype preferring ligands, having the formula:

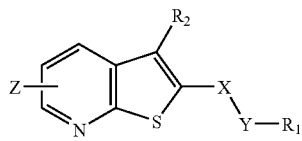

wherein $R_1$, $R_2$, X, Y and Z are as defined therein.

The compounds are stated to be useful in therapy and/or prevention of pathological conditions which require the modulation of mGluR1 and mGluR5 receptors such as neurological disorders, psychiatric disorders, acute and chronic pain and neuromuscular dysfunction of the lower urinary tract and gastrointestinal disorders.

SUMMARY OF THE INVENTION

The present invention relates to mGluR1 and mGluR5 receptor subtype preferring ligands of formula (I):

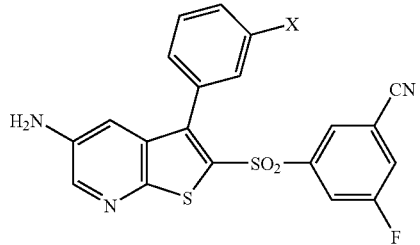

Wherein X is Cl or F; and/or hydrates and/or solvates and/or pharmaceutically acceptable salts thereof (i.e. or hydrates, solvates, or pharmaceutically acceptable salts, or combinations thereof).

Surprisingly, it has been found that these compounds have particularly desirable properties for therapeutically-applicable drugs useful in one or more of the treatment, therapy, or prevention of conditions relating to modulation of mGluR1 and mGluR5 receptors. For example, these compounds have favorable binding affinities to the mGluR5 receptor ($K_i$ values of less than about 10 nM), favorable anxiolytic activity in rats after oral administration (minimal effective doses of less than about 10 mg/kg p.o.), and the degree of oral bioavailability of these compounds in rodents exceeds 10.0%.

Other compounds falling within the scope of WO 2007/072095 (including structurally close analogues) were not found to meet the above three criteria.

This disclosure also provides processes for the synthesis of compounds of formula (I).

This disclosure also provides intermediates useful in the preparation process.

This disclosure also provides pharmaceutical compositions containing a therapeutically effective amount of at least one of: a compound of formula (I), or salts, hydrates, or solvates thereof (including combinations thereof) as active ingredient and at least one of: pharmaceutically acceptable diluents, excipients or inert carriers (including combinations thereof). For purposes of this disclosure, the phrase: "at least one of: a, b, or c" and the like also encompasses combinations of the listed selections, whether or not combinations is explicitly recited. This disclosure also provides for the use of a compound of formula (I) for the prevention, therapy, and/or treatment of mGluR5 receptor mediated disorders, such as neurological disorders, psychiatric disorders, acute and chronic pain and neuromuscular dysfunction of the lower urinary tract and gastrointestinal disorders.

This disclosure also provides for the use of a compound of formula (I) for the manufacture of a medicament for the prevention and/or treatment of mGluR5 receptor-mediated disorders, such as neurological disorders, psychiatric disorders, acute and chronic pain and neuromuscular dysfunction of the lower urinary tract and gastrointestinal disorders.

DETAILED DESCRIPTION OF THE INVENTION

The present invention relates to mGluR1 and mGluR5 receptor subtype preferring ligands of formula (I)

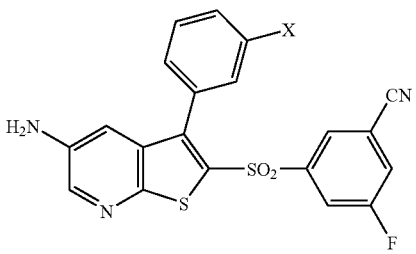

Wherein X is Cl or F; and/or hydrates and/or solvates and/or pharmaceutically acceptable salts thereof.

When X is F, the compound may be called:
5-Amino-2-(3-cyano-5-fluoro-benzenesulfonyl)-3-(3-fluorophenyl)-thieno[2,3-b]-pyridine
(Compound 1)

When X is Cl, the compound may be called:
5-Amino-2-(3-cyano-5-fluoro-benzenesulfonyl)-3-(3-chlorophenyl)-thieno[2,3-b]-pyridine
(Compound 2)

Compounds of formula (I) may form salts with acids. The invention relates also to the salts of compounds of formula (I) formed with acids, including without limitation the salts formed with pharmaceutically acceptable acids. The phrase "a compound of formula (I)" encompasses both the free base and the salt, even if the salt is not explicitly recited.

Both organic and inorganic acids can be used for the formation of acid addition salts. Suitable inorganic acids can be, for example, hydrochloric acid, sulfuric acid, nitric acid and phosphoric acid. Representatives of monovalent organic acids can be, for example, formic acid, acetic acid, propionic acid, and different butyric acids, valeric acids and capric acids. Representatives of bivalent organic acids can be, for example, oxalic acid, malonic acid, maleic acid, fumaric acid and succinic acid. Other organic acids can also be used, such as without limitation hydroxy acids, for example citric acid and tartaric acid, or aromatic carboxylic acids, for example, benzoic acid and salicylic acid, as well as aliphatic and aromatic sulfonic acids, for example, methanesulfonic acid, naphthalenesulfonic acid and p-toluenesulfonic acid. In some embodiments, the acid addition salts are ones in which the acid component itself is physiologically acceptable and does not have a therapeutic effect in the applied dose or it does not have unfavorable influence on the effect of the active ingredient. These acid addition salts are pharmaceutically acceptable acid addition salts. In some embodiments, the acid addition salts may not be pharmaceutically acceptable acid addition salts because, for example, they can be advantageous in the purification and isolation of the desired compounds.

In some embodiments, the compounds of formula (I) can be solvates and/or hydrates of compounds of formula (I).

Pharmaceutical Formulations

In some embodiment, the invention provides pharmaceutical compositions containing the compounds of formula (I) and/or physiologically acceptable salts and/or hydrates and/or solvates thereof as active ingredients and one or more physiologically acceptable carriers.

The compounds of formula (I) and/or physiologically acceptable salts and/or hydrates and/or solvates thereof may be administered by any convenient method, for example by oral, parenteral (including subcutaneous, intramuscular, and intravenous), buccal, sublingual, nasal, rectal or transdermal administration and the pharmaceutical compositions adapted accordingly.

The compounds of formula (I) and/or physiologically acceptable salts and/or hydrates and/or solvates thereof which are active when given orally can be formulated as liquids or solids, for example syrups, suspensions or emulsions, tablets, capsules and lozenges.

A liquid formulation of the compounds of formula (I) and/or physiologically acceptable salts and/or hydrates and/or solvates thereof generally include a suspension or solution of the compound of formula (I) and/or physiologically acceptable salts and/or hydrates and/or solvates thereof in a suitable liquid carrier(s), for example, an aqueous solvent, such as water and ethanol or glycerine, or a non-aqueous solvent, such as polyethylene glycol or an oil. The formulation may also contain a suspending agent, preservative, flavouring or colouring agent.

A composition in the solid form of a tablet can be prepared using any suitable pharmaceutical carrier(s) routinely used for preparing solid formulations. Examples of solid carriers include lactose, terra alba, sucrose, talc, gelatine, agar, pectin, acacia, magnesium stearate, and stearic acid, etc. Optionally, tablets may be coated by standard aqueous or nonaqueous techniques.

A composition in the solid form of a capsule can be prepared using routine encapsulation procedures. For example, pellets containing the active ingredient can be prepared using standard carriers and then these can be filled into a hard gelatine capsule; alternatively, a dispersion or suspension can be prepared using any suitable pharmaceutical carrier(s), for example, aqueous gums, celluloses, silicates or oils and the dispersion or suspension can then be filled into a soft gelatine capsule.

Parenteral compositions may be a solution or suspension of the compound of formula (I) and/or physiologically acceptable salts and/or hydrates and/or solvates thereof in a sterile aqueous carrier or parenterally acceptable oil, for example, polyethylene glycol, polyvinyl pyrrolidone, lecithin, arachis oil and sesame oil. Alternatively, the solution can be lyophilised and then reconstituted with a suitable solvent just prior to administration.

In some embodiments, compositions including one or more compounds according to the present invention may be formulated for nasal administration. For example, a nasal administration formulation may include a compound of formula (I) and/or physiologically acceptable salts and/or hydrates and/or solvates thereof formulated as aerosols, drops, gels and powders. Aerosol formulations of the present invention may comprise a solution or fine suspension of the compound of formula (I) and/or physiologically acceptable salts and/or hydrates and/or solvates in a physiologically acceptable aqueous or non-aqueous solvent and may be presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal once the contents of the container have been exhausted. If the dosage form comprises an aerosol dispenser, it may contain a propellant which can be a compressed gas, such as compressed air or an organic propellant, such as a fluorochlorohydrocarbon. The aerosol dosage form can also take the form of a pump-atomiser.

In some embodiments, compositions including one or more compounds according to the invention may be formulated for buccal or sublingual administration. Such compositions may include a compound of formula (I) and/or physiologically acceptable salts and/or hydrates and/or solvates in the form of, for example, tablets, lozenges and pastilles, wherein the active ingredient is formulated with a carrier, such as sugar and acacia, tragacanth, gelatine, or glycerin, etc.

In some embodiments, compositions including one or more compounds according to the present invention may be formulated for rectal administration. Such compositions include a compound of formula (I) and/or physiologically acceptable salts and/or hydrates and/or solvates thereof in the form of suppositories containing a conventional suppository base, such as cocoa butter and other materials commonly used in the art. The suppositories may be conveniently formed by first admixing the composition with the softened or melted carrier(s) followed by chilling and shaping in moulds.

In some embodiments, compositions including one or more compounds according to the invention may be formulated for transdermal administration. Such compositions can include a compound of formula (I) and/or physiologically acceptable salts and/or hydrates and/or solvates thereof formulated in ointments, gels or patches.

In some embodiments, compositions of the present invention including a compound of formula (I) and/or physiologically acceptable salts and/or hydrates and/or solvates thereof can be in the unit dose form, such as a tablet, capsule or ampoule.

In some embodiments, each dosage unit of the present invention for oral administration contains from about 0.1 to about 500 mg of a compound of formula (I) and/or physiologically acceptable salts and/or hydrates and/or solvates thereof calculated as a free base.

In some embodiments, each dosage unit of the present invention for parenteral administration contains from about 0.1 to about 500 mg of a compound of formula (I) and/or physiologically acceptable salts and/or hydrates and/or solvates thereof calculated as a free base.

The compounds of formula (I) and/or physiologically acceptable salts and/or hydrates and/or solvates thereof may be administered in a daily dosage regimen. In the treatment of mGluR1 and mGluR5 mediated disorders, such as schizophrenia, anxiety, depression, panic, bipolar disorders, and circadian disorders or chronic and acute pain disorders the dosage levels from about 0.01 mg/kg to about 100 mg/kg of body weight per day may be suitable or alternatively about 0.5 mg to about 7 g per patient per day.

The amount of active ingredient that may be combined with the carrier materials to produce a single dosage form may vary depending upon the host treated and the particular mode of administration. For example, a formulation intended for oral administration to humans may conveniently contain from about 0.5 mg to about 5 g of active agent, compounded with an appropriate and convenient amount of carrier material which may vary from about 5 to about 95 percent of the total composition. Unit dosage forms may generally contain between from about 1 mg to about 1000 mg of the active ingredient, for example, 25 mg, 50 mg, 100 mg, 200 mg, 250 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Medical Use

The compounds of formula (I) and/or physiologically acceptable salts and/or hydrates and/or solvates of the present invention have been found to exhibit biological activity at mGluR1 and mGluR5 receptors and are expected to be useful in the treatment of mGluR1 and mGluR5 mediated disorders.

It has been found that the compounds according to the present invention or salts thereof, exhibit a high degree of potency and selectivity for mGluR1 and mGluR5 receptors. In particular, the compounds according to the present invention are highly potent (K<10 mM) ligands of the mGluR5 receptor. Accordingly, the compounds of the present invention are expected to be useful in the prevention and/or treatment of conditions associated with excitatory activation of mGluR1 and mGluR5 receptors. The compounds may be used to produce an inhibitory effect of mGluR1 and mGluR5, in mammals, including humans.

Furthermore, compounds of the present invention showed favorable bioavailability (>10.0%) and potent in vivo activity (MED<10 mg/kg p.o.) after oral administration in animal assays. Accordingly, the compounds of the present invention are expected to be particularly suitable for oral application in conditions relating to the modulation of mGluR1 and mGluR5 receptors.

Thus, it is expected that the compounds of the present invention are well suited for the prevention, therapy and/or treatment of mGluR1 and mGluR5 receptor-mediated disorders such as acute and chronic neurological and psychiatric disorders, chronic and acute pain disorders and neuromuscular dysfunction of the lower urinary tract and gastrointestinal disorders.

The dose required for the therapeutic or preventive treatment of a particular disorder may be varied depending on the host treated and the route of administration.

In some embodiments, the invention relates to compounds of formula (I) as defined hereinbefore, for use in therapy.

In some embodiments, the invention relates to compounds of formula (I) as defined hereinbefore, for use in therapy, prevention and/or treatment of mGluR1 and mGluR5 receptor-mediated disorders.

In some embodiments, the invention relates to compounds of formula (I) as defined hereinbefore, for use in therapy, prevention and/or treatment of neurological disorders.

In some embodiments, the invention relates to compounds of formula (I) as defined hereinbefore, for use in therapy, prevention and/or treatment of psychiatric disorders.

In some embodiments, the invention relates to compounds of formula (I) as defined hereinbefore, for use in therapy, prevention and/or treatment of chronic and acute pain disorders.

In some embodiments, the invention relates to compounds of formula (I) as defined hereinbefore, for use in therapy, prevention and/or treatment of neuromuscular dysfunction of the lower urinary tract and gastrointestinal disorders.

In some embodiments, the invention relates to compounds of formula (I) as defined hereinbefore, for use in therapy, prevention and/or treatment of pain related to migraine, inflammatory pain, neuropathic pain disorders such as diabetic neuropathies, arthritis and rheumatoid diseases, low back pain, post-operative pain and pain associated with various conditions including angina, in renal or biliary colic, menstruation, migraine and gout.

In some embodiments, the invention relates to compounds of formula (I) as defined hereinbefore, for use in therapy, prevention and/or treatment of Alzheimer's disease, senile dementia, AIDS-induced dementia, Parkinson's disease, amyotrophic lateral sclerosis, Huntington's Chorea, migraine, epilepsy, schizophrenia, depression, anxiety, acute anxiety, obesity, obsessive compulsive disorder, attention deficit and hyperactivity disorder, substance abuse and dependence, opthalmological disorders such as retinopathies, diabetic retinopathies, glaucoma, auditory neuropathic disorders such as tinnitus, chemotherapy induced neuropathies, post-herpetic neuralgia and trigeminal neuralgia, Fragile X, autism, mental retardation, and Down's Syndrome.

In some embodiments, the invention relates to compounds of formula (I) as defined hereinbefore, for use in therapy, prevention and/or treatment of stroke, head trauma, anoxic and ischemic injuries, hypoglycemia, cardiovascular diseases, and epilepsy.

The one or all of the compounds may be well suited for the treatment of neuromuscular dysfunction of the lower urinary tract, such as urinary urgency, overactive bladder, greater urinary frequency, reduced urinary compliance, cystitis, incontinence, enuresis, and dysuria.

Furthermore, one or all of the compounds may be well suited for the treatment of gastrointestinal disorders, such as transient lower esophageal sphincter relaxation (TLESR), gastrointestinal reflux disease and irritable bowel syndrome.

In some embodiments, the present invention relates also to the use of a compound of formula (I) as defined hereinbefore, in the manufacture of a medicament for therapy, prevention and/or treatment of mGluR1 and mGluR5 receptor-mediated disorders and any disorder listed above.

In some embodiments, the invention also provides a method of therapy, treatment and/or prevention of mGluR1 and mGluR5 receptor mediated disorders and any disorder listed above, in a patient suffering from, or at risk of, said condition, which comprises administering to the patient an effective amount of a compound of formula (I), as hereinbefore defined.

In this specification, the term "about" is intended to encompass the range of experimental error associated with a particular measurement.

In this specification, unless stated otherwise, the term "antagonist" means a compound that by any means, partly or completely blocks the transduction pathway leading to the production of a response by the ligand.

The term "disorder", unless stated otherwise, means any condition or disease associated with metabotropic glutamate receptor activity.

Methods of Preparation

The disclosure provides a process for the preparation of a compound of formula (I)

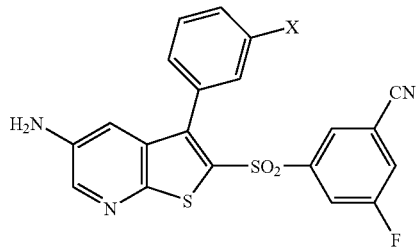

wherein X is Cl or F; and/or hydrates and/or solvates and/or pharmaceutically acceptable salts thereof, illustrated schematically below wherein X is Cl or F; and/or hydrates and/or solvates and/or pharmaceutically acceptable salts thereof, illustrated schematically below.

Scheme:

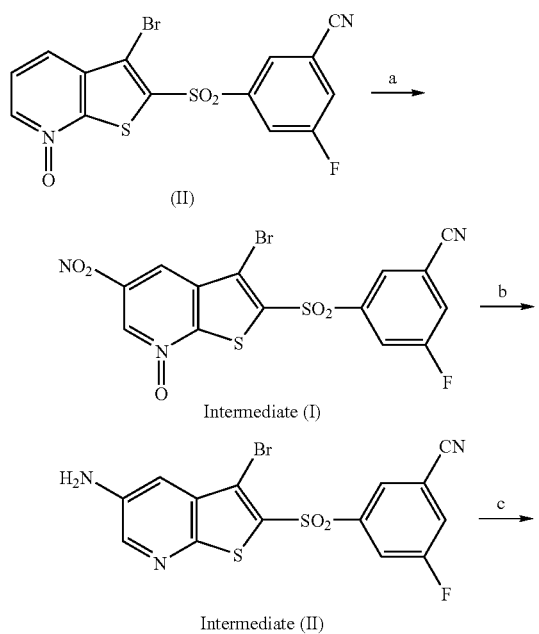

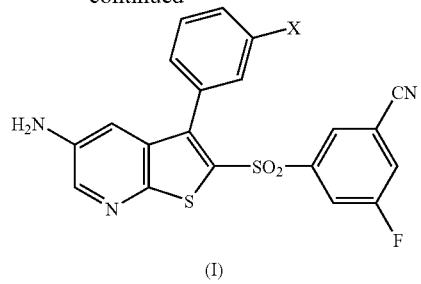

a.) aq. $HNO_3$-acetic acid, 100-130° C., 4-6 hrs;
b.) Fe powder-acetic acid, 60-70° C., 1 h;
c.) 3-Cl or 3-F-phenylboronic acid, toluene-ethanol/2M $NaCO_3$ aq. solution, reflux, 1 h.

In some embodiments, a compound of formula (I) can be prepared from the precursor compound of formula (II) by nitration, followed by reduction and Suzuki coupling.

In some embodiments, salts and/or hydrates and/or solvates of compounds of formula (I) can be formed.

Intermediate (I) was prepared from the corresponding N-oxide (II) (WO 2007/072095) by a selective nitration reaction using aq. nitric acid in acetic acid. The reaction was carried out in the range of 100-130° C. temperature by the method of Klemm, L. H (*J. Heterocycl. Chem.*, 7, 1970, 81).

Intermediate (II) was selectively reduced with iron used in combination with acid (HCl or preferably acetic acid) by the method of *Org. Synth. Coll.*, 5, 346, 1973.

Compounds of formula (I) were synthesised by the well known methods of Suzuki coupling reactions using the appropriate boronic acid, base and palladium catalyst as described, for example, in A. Suzuki & H. C. Brown: *Organic Syntheses via Boranes* Vol. 1-3.

Biological Test Methods

MGluR5 Receptor Binding Tests

MGluR5 receptor binding was determined according to Gasparini et al. (*Bioorg. Med. Chem. Lett.* 2000, 12:407-409) with modifications. Rat cerebro-cortical membrane preparation was used to determine the binding characteristics of reference compounds and novel compounds to the rat mGluR5. The A18 cell line expressing hmGluR5a (purchased from Euroscreen) was used to determine binding characteristics of the chemical compounds to the human mGluR5a receptor. [3H]-M-MPEP (2 nM) was used as a radioligand. The nonspecific binding was determined in the presence of 10 µM M-MPEP.

Measurement of Anxiolytic Activity in the Punished Drinking Test

The method described by Vogel et al. (*Psychopharmacology (Berl.)* 1971, 21:1-7) was used with modifications. On the day preceding the test day male Wistar rats (180-220 g) were placed into the test chambers which were equipped with a metal water spout mounted on the wall of the chamber and a metal grid floor for delivering electric shocks. During a 5-min adaptation period the animals had free access to the drinking spout. Following the adaptation session rats were deprived of drinking water for 24 hours prior to the test. On the day of the measurement, the animals were orally treated with the test compounds and 60 minutes later were placed into the test chambers where they had access to the drinking water. In the test session drinking was punished by delivering electric shocks (1 mA, 1 sec) through the drinking spout following every 10 licks during a 270 second punishment period. Number of licks and shocks delivered were recorded and stored in a computer. Anxiolytic activity is reflected by the increased number of accepted shocks. Minimum effective doses (MED, defined as the dose which increased the number of accepted shocks above 35) were determined and used to characterize the anxiolytic potency of the tested compounds.

Determination of Oral Bioavailability

The oral bioavailability study was performed in male Wistar rats (200-220 g, n=4) fasted overnight. The compounds were formulated freshly as a microemulsion for intravenous dosing and as a suspension for oral dosing. A dose of 3 mg/kg of the compounds was administered intravenously in the tail vein by a dosing volume of 2.5 ml/kg. Blood samples (~1 ml) were drawn from the retroorbital sinus at 0.083, 0.333, 1.0, 5.0 hour post-dose into heparinized tubes. A dose of 10 mg/kg of the compounds were administered orally to rats by a dosing volume of 5 ml/kg by gavage. Blood samples (~1 ml) were drawn from the retroorbital sinus at 0.4, 1.0, 2.0, 5.0 hours post-dose into heparinized tubes.

Plasma samples were obtained by immediate centrifugation of blood samples and were stored at −20° C. until HPLC-UV analysis.

Plasma samples were extracted with chlorobutane and then analysed on 150×4.6 mm, 5 μm, Zorbax Eclipse XDB-C18 column (Agilent) using gradient elution with binary mobile phase containing 0.1 M ammonium acetate and acetonitrile. Analysis were performed at 40° C. The column eluent was monitored at 245 nm (Compound 2) and 250 nm (Compound 1).

The pharmacokinetic parameters (AUC, $C_{max}$, $t_{max}$ were calculated by non-compartmental analysis using Kinetica Version 4.4.1 Program. The absolute oral bioavailability was calculated as $AUC_{oral}/AUC_{iv} \cdot Dose_{iv}/Dose_{oral}$.

Results

| Assay | Compound 1 | Compound 2 |
|---|---|---|
| rat mGluR5 binding, $K_i$ (nM) | 1.9 | 7.2 |
| human mGluR5a binding, $K_i$ (nM) | 3.2 | 8.7 |
| Punished drinking, MED (mg/kg) | 3 | 5 |
| oral bioavailbility (%) | 10.2 | 13.4 |

Compound 1 and Compound 2 bind with high affinity to both human and rat mGlu5 receptors. The compounds showed remarkable anxiolytic activity after oral administration and their oral bioavailability exceeds 10.0%. These pharmacological properties represents definite advantage in terms of drug-like properties and treatment, therapeutic or preventive applicability and renders Compound 1 and Compound 2 particularly suitable for oral application in conditions which require the modulation of mGluR1 and mGluR5 receptors.

The following examples are intended to illustrate but not to limit the invention in any manner, shape, or form, either explicity or implicity.

EXAMPLES

Intermediate 1

3-Bromo-2-(3-cyano-5-fluoro-benzenesulfonyl)-5-nitro-thieno[2,3-b]pyridin-N-oxide

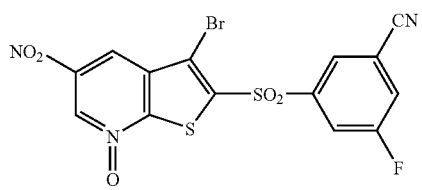

3-Bromo-2-(3-cyano5-fluorobenzenesulfonyl)-thieno[2,3-b]pyridin-N-oxide (prepared as described in WO 2007/072095) (7.97 g, 19.3 mmol) was boiled at 120° C. with 66% nitric acid (1.22 ml) in acetic acid (25 ml) for 4 hours. The reaction mixture was evaporated and the residue was purified by chromatography (Kieselgel 60, chloroform:methanol=5:0.1). First the starting material was isolated (3.7 g, 47%), than a yellow solid, which was treated with ether (5 ml). After filtration the title compound was isolated (0.72 g, 8.3%). LC-MS: $(M+H)^+$ 459.1.

Intermediate 2

5-Amino 3-bromo-2-(3-cyano-5-fluoro-benzene-sulfonyl)-thieno[2,3-b]pyridine

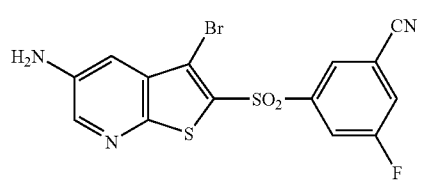

3-Bromo-2-(3-cyano-5-fluoro-benzenesulfonyl)-5-nitro-thieno[2,3-b]pyridin-N-oxide (1.0 g, 2.18 mmol) was suspended in acetic acid (12 ml) and Fe powder was added (0.73 g, 13 mmol). The reaction mixture was stirred at 60-70° C. for 60 minutes. Chloroform (45 ml) was added and after filtration through celite the filtrate was evaporated, the crude residue was treated with methanol (3 ml). The product was filtered, washed with methanol. It was obtained (0.69 g, 76.7%) as a yellow powder. LC-MS: (M+H)+ 413.1.

Example 1

5-Amino-2-(3-cyano-5-fluoro-benzenesulfonyl)-3-(3-fluorophenyl)-thieno[2,3-b]-pyridine

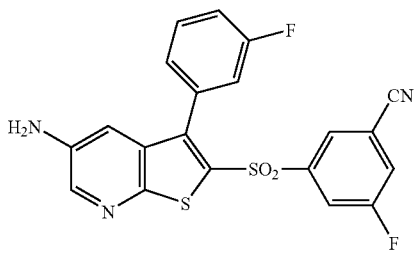

5-Amino-3-bromo-2-(3-cyano-5-fluoro-benzenesulfonyl)-thieno[2,3-b]pyridine (1.2 g, 29 mmol) was dissolved in toluene (16 ml) and ethanol (18 ml) under argon atmosphere. To the solution Pd(PPh$_3$)$_4$ (157 mg, 0.14 mmol), 3-fluorophenylboronic acid (0.50 g, 35.8 mmol) and 2M solution of Na$_2$CO$_3$ (14 ml) was added. The reaction mixture was refluxed for 1 hour then it was filtered through celite and washed with toluene. The filtrate was tightened in vacuum; water (13 ml) and ethyl acetate (13 ml) were added to the residue. It was separated and the water phase was extracted with ethyl acetate (2×5 ml). The organic phase was washed with water (5.0 ml), dried over Na$_2$SO$_4$, filtered, and concentrated in vacuo. The crude product was purified by column chromatography (Kieselgel 60, ethyl acetate:hexane=2:1) to yield 0.94 g (76%) of the title compound. The crude product can be purified by stirring with methanol to give a yellow amorphous material. LC-MS: (M+H)+ 428.2. $^1$H NMR (500 MHz, DMSO-d$_6$, 25° C.): 5.67 (s, 2H); 6.81 (d, J=2.6 Hz, 1H); 7.00-7.07 (m, 2H); 7.35-7.43 (m, 1H); 7.50-7.60 (m, 2H); 7.60-7.64 (m, 1H); 8.20-8.25 (m, 1H); 8.27 (d, J=2.6 Hz, 1H).

Example 2

5-Amino-2-(3-cyano-5-fluoro-benzenesulfonyl)-3-(3-chlorophenyl)-thieno[2,3-b]-pyridine

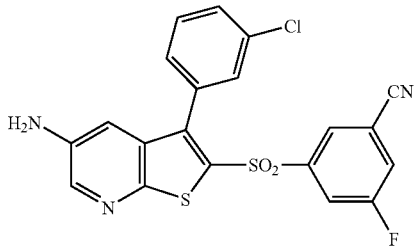

5-Amino-3-bromo-2-(3-cyano-5-fluoro-benzenesulfonyl)-thieno[2,3-b]pyridine (1.25 g, 30 mmol) was dissolved in toluene (18 ml) and ethanol (20 ml) under argon atmosphere. To the solution Pd(PPh$_3$)$_4$ (175 mg, 0.15 mmol), 3-chlorophenylboronic acid (0.58 g, 37 mmol) and 2M solution of Na$_2$CO$_3$ (15 ml) was added. The reaction mixture was refluxed for 1 hour then it was filtered through celite and washed with toluene (2×5 ml). The filtrate was tightened in vacuum; water (13 ml) and ethyl acetate (13 ml) were added to the residue. It was separated and the water phase was extracted with ethyl acetate (2×5 ml). The organic phase was washed with water (5.0 ml), dried over Na$_2$SO$_4$, filtered, and concentrated under vacuum. The crude product was purified by column chromatography (Kieselgel 60, ethyl acetate:hexane=2:1) to yield the title compound which was purified by stirring with methanol (5 ml) to give 0.84 g (63%) yellow amorphous material. LC-MS: (M+H)+ 444.2. $^1$H NMR (400 MHz, DMSO-d$_6$, 25° C.): 5.68 (s, 2H); 6.80 (d, J=2.6 Hz, 1H); 7.13-7.22 (m, 2H); 7.53 (t, J=7.9 Hz, 1H); 7.56-7.65 (m, 3H); 8.24 (dm, J=8.4 Hz, 1H); 8.27 (d, J=2.6 Hz, 1H).

$^1$H NMR spectra were obtained on a Varian V-500 or a Varian V-400 spectrometer. Chemical shifts are reported in parts per million relative to TMS as internal standard.

Example 3

Preparation of Pharmaceutical Compositions a) Tablets:

0.01-50% of the active ingredient of formula (I), 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin were mixed, then granulated by wet granulation and pressed to tablets.

b) Dragées, Film Coated Tablets:

The tablets made according to the method described above were coated by a layer consisting of entero- or gastrosolvent film, or of sugar and talc. The dragées were polished by a mixture of beeswax and carnuba wax.

c) Capsules:

0.01-50% of the active ingredient of formula (I), 1-5% of sodium lauryl sulfate, 15-50% of starch, 15-50% of lactose, 1-3% of colloid silicon dioxide and 0.01-3% of magnesium stearate were thoroughly mixed, the mixture was passed through a sieve and filled in hard gelatin capsules.

d) Suspensions:

Ingredients: 0.01-15% of the active ingredient of formula (I), 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To a solution of nipagin and citric acid in 20 ml of distilled water, carbopol was added in small portions under vigorous stirring, and the solution was left to stand for 10-12 hours. Then the sodium hydroxide in 1 ml of distilled water, the aqueous solution of sorbitol and finally the ethanolic raspberry flavor were added with stirring. To this carrier the active ingredient was added in small portions and suspended with an immersing homogenizator. Finally, the suspension was filled up to the desired final volume with distilled water and the suspension syrup was passed through a colloid milling equipment.

e) Suppositories:

For each suppository 0.01-15% of the active ingredient of formula (I) and 1-20% of lactose were thoroughly mixed, then 50-95% of adeps pro suppository (for example Witepsol 4) was melted, cooled to 35° C. and the mixture of active ingredient and lactose was mixed in it with a homogenizator. The obtained mixture was moulded in cooled forms.

f) Lyophilized Powder Ampoule Compositions:

A 5% solution of mannitol or lactose was made with bidistilled water for injection use, and the solution was filtered so as to have a sterile solution. A 0.01-5% solution of the active ingredient of formula (I) was also made with bidistilled water for injection use, and this solution was filtered so as to have a sterile solution. These two solutions were mixed under aseptic conditions, filled in 1 ml portions into ampoules, the content of the ampoules was lyophilized, and the ampoules were sealed under nitrogen. The contents of the ampoules were dissolved in sterile water or 0.9% (physiological) sterile aqueous sodium chloride solution before administration.

The invention claimed is:

1. A compound of formula (I):

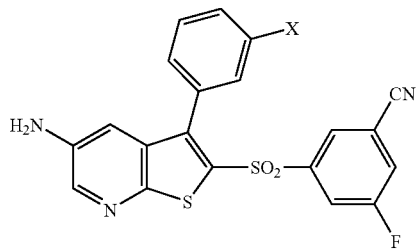

or a pharmaceutically acceptable salt thereof,
wherein X is Cl or F.

2. A compound according to claim 1, wherein the compound is in the form of a pharmaceutically acceptable salt.

3. A compound:
5-Amino-2-(3-cyano-5-fluoro-benzenesulfonyl)-3-(3-fluorophenyl)-thieno[2,3-b]-pyridine or a pharmaceutically acceptable salt thereof.

4. A process for the preparation of a compound of formula (I):

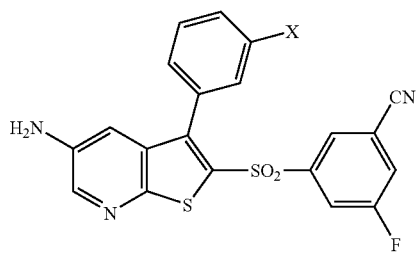

or a pharmaceutically acceptable salt thereof,
wherein X is Cl or F; comprising:
nitration of a compound of formula (II);

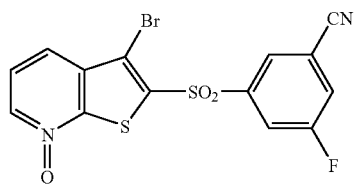

followed by a reduction and then a Suzuki coupling reaction to obtain a compound of formula (I).

5. A process according to claim 4, wherein the process comprises preparing a pharmaceutically acceptable salt of the compound of formula (1).

6. A process according to claim 4, wherein the nitration produces an intermediate of formula (I):

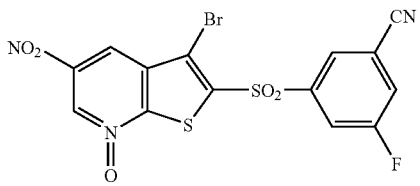

the reduction reaction reduces the intermediate of formula (I) to produce an intermediate of formula (II):

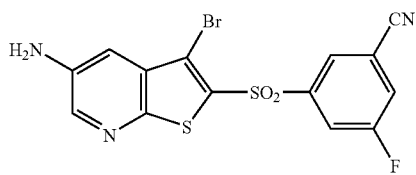

and the Suzuki coupling reaction is of the intermediate of formula (II) to produce the compound of formula (I).

7. A pharmaceutical formulation, comprising: a therapeutically-effective amount of a compound of formula (I)

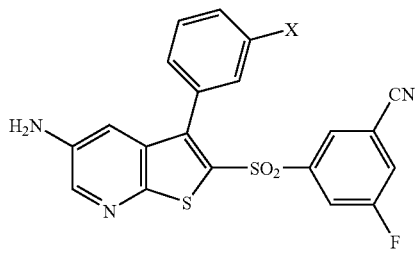

or a pharmaceutically acceptable salt thereof,
wherein X is Cl or F;
and at least one of physiologically acceptable diluents, excipients or inert carriers.

8. A pharmaceutical composition according to claim 7, wherein the compound is in the form of a pharmaceutically acceptable salt.

9. A compound:
5-Amino-2-(3-cyano-5-fluoro-benzenesulfonyl)-3-(3-chlorophenyl)-thieno[2,3-b]-pyridine, or a pharmaceutically acceptable salt thereof.

10. A compound according to claim 1, wherein the compound is in the form of a pharmaceutically acceptable salt.

11. A compound according to claim 3, wherein the compound is in the form of a pharmaceutically acceptable salt.

12. A compound according to claim 9, wherein the compound is in the form of a pharmaceutically acceptable salt.

13. A pharmaceutical formulation, comprising: 5-Amino-2-(3-cyano-5-fluoro-benzenesulfonyl)-3-(3-fluorophenyl)-thieno[2,3-b]-pyridine or a pharmaceutically acceptable salt thereof, and at least one of physiologically acceptable diluents, excipients or inert carriers.

14. A pharmaceutical composition according to claim 13, wherein the compound is in the form of a pharmaceutically acceptable salt.

15. A pharmaceutical formulation, comprising: 5-Amino-2-(3-cyano-5-fluoro-benzenesulfonyl)-3-(3-chlorophenyl)-thieno[2,3-b]-pyridine or a pharmaceutically acceptable salt thereof, and at least one of physiologically acceptable diluents, excipients or inert carriers.

16. A pharmaceutical composition according to claim 15, wherein the compound is in the form of a pharmaceutically acceptable salt.

* * * * *